(12) United States Patent
Palmer et al.

(10) Patent No.: US 10,302,600 B2
(45) Date of Patent: May 28, 2019

(54) INSPECTION DEVICES AND RELATED SYSTEMS AND METHODS

(71) Applicant: Northrop Grumman Innovation Systems, Inc., Plymouth, MN (US)

(72) Inventors: Jeremy D. Palmer, Farmington, UT (US); Ronald G. Mellus, Erda, UT (US); Edwin Dean S. Oba, Holladay, UT (US)

(73) Assignee: Northrop Grumman Innovation Systems, Inc., Plymouth, MN (US)

( * ) Notice: Subject to any disclaimer, the term of this patent is extended or adjusted under 35 U.S.C. 154(b) by 572 days.

(21) Appl. No.: 15/000,921

(22) Filed: Jan. 19, 2016

(65) Prior Publication Data
US 2017/0205381 A1  Jul. 20, 2017

(51) Int. Cl.
*G01N 29/28* (2006.01)
*G01N 29/11* (2006.01)
*G01N 29/22* (2006.01)

(52) U.S. Cl.
CPC ............. *G01N 29/28* (2013.01); *G01N 29/11* (2013.01); *G01N 29/221* (2013.01); *G01N 29/223* (2013.01); *G01N 2291/0231* (2013.01)

(58) Field of Classification Search
CPC ...... G01N 29/28; G01N 29/11; G01N 29/221; G01N 29/223; G01N 2291/0231
USPC .................................................. 73/627, 644
See application file for complete search history.

(56) References Cited

U.S. PATENT DOCUMENTS

| | | |
|---|---|---|
| 3,453,872 A | 7/1969 | Botsco |
| 3,550,438 A | 12/1970 | Kapluszak |
| 4,156,228 A | 5/1979 | Heckman |
| 4,304,133 A | 12/1981 | Feamster, III |
| 4,375,818 A | 3/1983 | Suwaki et al. |
| 4,726,231 A | 2/1988 | Tretout et al. |
| 4,776,904 A | 10/1988 | Charlton et al. |
| 4,848,159 A | 7/1989 | Kennedy et al. |
| 4,881,177 A | 11/1989 | McClean et al. |
| 4,986,135 A | 1/1991 | Corser et al. |

(Continued)

FOREIGN PATENT DOCUMENTS

| | | |
|---|---|---|
| CN | 103962890 A | 8/2014 |
| CN | 105642491 A | 6/2016 |

(Continued)

OTHER PUBLICATIONS

Inspection Technologies: Standard Phased Array Probes and Accessories, GE Measurement and Control [online] GEIT-20122EN Nov. 2012 [retrieved on Aug. 29, 2013] retrieved on the Internet at <http://www.gemcs.com/transselection-guide/brochures/GEIT 20122EN Standard Catalogus.pdf> 28 pages.

(Continued)

*Primary Examiner* — Justin Seo
*Assistant Examiner* — Rose M Miller
(74) *Attorney, Agent, or Firm* — TraskBritt

(57) ABSTRACT

Inspection devices include a nozzle portion having at least one opening and a transducer disposed in a rear chamber of the housing. The housing has at least one fluid channel defined in the housing and extending along at least a portion of the rear chamber. The at least one fluid channel is configured to supply a fluid into a forward chamber of the housing proximate the transducer. Related methods include operating an inspection device.

25 Claims, 6 Drawing Sheets

(56) References Cited

U.S. PATENT DOCUMENTS

| | | |
|---|---|---|
| 5,001,932 A | 3/1991 | Light et al. |
| 5,282,472 A | 2/1994 | Companion et al. |
| 5,372,043 A | 12/1994 | Speight, II et al. |
| 5,398,216 A | 3/1995 | Hall et al. |
| 5,485,751 A | 1/1996 | Karbach et al. |
| 5,493,912 A * | 2/1996 | Gunther ............... G01N 29/28 73/644 |
| 5,535,628 A | 7/1996 | Rutherford |
| 5,596,989 A | 1/1997 | Morita |
| 5,623,107 A | 4/1997 | Patterson, Sr. et al. |
| 5,698,787 A | 12/1997 | Parzuchowski et al. |
| 6,220,099 B1 | 4/2001 | Marti et al. |
| 6,315,565 B1 | 11/2001 | Slotke et al. |
| 6,974,417 B2 | 12/2005 | Lockwood et al. |
| 7,176,681 B2 | 2/2007 | Zombo |
| 7,404,327 B2 * | 7/2008 | Barco Villalba ....... G01N 29/28 73/644 |
| 7,464,596 B2 | 12/2008 | Bui et al. |
| 7,467,052 B2 | 12/2008 | Vaccaro |
| 7,516,664 B2 | 4/2009 | Meier et al. |
| 7,571,649 B2 | 8/2009 | Young |
| 7,640,811 B2 | 1/2010 | Kennedy et al. |
| 7,703,327 B2 | 4/2010 | Georgeson et al. |
| 7,836,768 B2 | 11/2010 | Young et al. |
| 8,082,793 B2 | 12/2011 | Sarr et al. |
| 8,087,298 B1 | 1/2012 | DiMambro et al. |
| 8,156,811 B2 | 4/2012 | Toller et al. |
| 8,270,254 B2 | 9/2012 | Casula |
| 8,347,746 B2 | 1/2013 | Hafenrichter et al. |
| 8,371,173 B1 | 2/2013 | DiMambro et al. |
| 8,438,928 B2 | 5/2013 | Frederick et al. |
| 8,521,446 B2 | 8/2013 | Zhang et al. |
| 8,525,831 B2 | 9/2013 | Zhang et al. |
| 8,578,779 B2 | 11/2013 | Bond-Thorley |
| 8,839,673 B2 | 9/2014 | Rasselkorde et al. |
| 8,894,787 B2 | 11/2014 | Boe |
| 8,997,573 B2 | 4/2015 | Wright |
| 9,031,734 B2 | 5/2015 | Froom |
| 9,037,419 B2 | 5/2015 | Na et al. |
| 9,091,638 B2 | 7/2015 | Frederick et al. |
| 2003/0067249 A1 | 4/2003 | Lockwood et al. |
| 2006/0206025 A1 | 9/2006 | Zombo |
| 2007/0118313 A1 | 5/2007 | Vaccaro |
| 2007/0171508 A1 | 7/2007 | Huibers |
| 2007/0227250 A1 | 10/2007 | Kennedy et al. |
| 2008/0257048 A1 | 10/2008 | Walters et al. |
| 2009/0126496 A1 * | 5/2009 | Maurer ............... G01N 29/28 73/644 |
| 2009/0211361 A1 | 8/2009 | Young et al. |
| 2010/0132597 A2 | 6/2010 | Ries |
| 2010/0139404 A1 | 6/2010 | Tapia et al. |
| 2010/0171518 A1 | 7/2010 | Bateman et al. |
| 2010/0329081 A1 | 12/2010 | Sullivan et al. |
| 2011/0032800 A1 | 2/2011 | Casula |
| 2011/0100128 A1 | 5/2011 | Bond-Thorley |
| 2011/0109627 A1 | 5/2011 | Zhang et al. |
| 2011/0126628 A1 | 6/2011 | Oberdorfer et al. |
| 2011/0178727 A1 | 7/2011 | Hafenrichter et al. |
| 2011/0277549 A1 | 11/2011 | Frederick et al. |
| 2012/0130653 A1 | 5/2012 | Zhang et al. |
| 2013/0167646 A1 | 7/2013 | Frederick et al. |
| 2013/0261876 A1 | 10/2013 | Froom et al. |
| 2013/0291640 A1 | 11/2013 | Rasselkorde et al. |
| 2013/0291641 A1 | 11/2013 | Wright |
| 2014/0053975 A1 | 2/2014 | Boe |
| 2014/0165730 A1 | 6/2014 | Na et al. |
| 2014/0216160 A1 | 8/2014 | Renzel |
| 2014/0260629 A1 | 9/2014 | Jaramillo et al. |
| 2014/0260630 A1 | 9/2014 | Thomson et al. |
| 2014/0278292 A1 | 9/2014 | Grellou et al. |
| 2014/0283612 A1 | 9/2014 | Williams et al. |
| 2015/0096382 A1 | 4/2015 | Voor, Jr. |
| 2015/0134274 A1 | 5/2015 | Froom et al. |
| 2015/0177194 A1 | 6/2015 | Xu et al. |
| 2015/0253288 A1 | 9/2015 | Spencer et al. |

FOREIGN PATENT DOCUMENTS

| | | |
|---|---|---|
| DE | 4233958 A1 | 4/1994 |
| DE | 102005020469 | 11/2005 |
| DE | 102008002859 A1 | 12/2009 |
| DE | 102008030688 A1 | 1/2010 |
| DE | 102011051546 A1 | 1/2013 |
| DE | 102013209807 A1 | 11/2014 |
| EP | 0209032 A2 | 1/1987 |
| EP | 0538110 A1 | 4/1993 |
| EP | 1057012 B1 | 11/2003 |
| EP | 2010377 B1 | 1/2011 |
| EP | 2345881 A1 | 7/2011 |
| EP | 1368633 B1 | 10/2012 |
| EP | 2605009 | 6/2013 |
| EP | 2738553 A1 | 6/2014 |
| EP | 2778672 A1 | 9/2014 |
| EP | 2829994 A2 | 1/2015 |
| EP | 1952137 B1 | 8/2015 |
| FR | 2995556 B1 | 10/2014 |
| FR | 3013455 A1 | 5/2015 |
| GB | 1535831 A | 12/1978 |
| GB | 2193574 B | 2/1988 |
| JP | 60033048 A | 2/1985 |
| JP | 62022063 A | 1/1987 |
| JP | 01054349 A | 3/1989 |
| JP | 04009149 A | 1/1992 |
| JP | 08062156 A | 3/1996 |
| JP | 10038864 A | 2/1998 |
| JP | 10510053 A | 9/1998 |
| JP | 2003090829 A | 3/2003 |
| JP | 2003177117 A | 6/2003 |
| JP | 2005055197 A | 3/2005 |
| JP | 3709559 B2 | 10/2005 |
| JP | 3749929 B2 | 3/2006 |
| JP | 2007512530 A | 5/2007 |
| JP | 2007218915 A | 8/2007 |
| JP | 4012930 B1 | 11/2007 |
| JP | 2008126218 A | 6/2008 |
| JP | 2008139304 | 6/2008 |
| JP | 2008248457 A | 10/2008 |
| JP | 2009108607 A | 5/2009 |
| JP | 2009544224 A | 12/2009 |
| JP | 2010117329 A | 5/2010 |
| JP | 2011519025 A | 6/2011 |
| JP | 2011529170 A | 12/2011 |
| JP | 2012107991 A | 6/2012 |
| JP | 2014013172 A | 1/2014 |
| JP | 5419424 B2 | 2/2014 |
| JP | 5454861 B2 | 3/2014 |
| JP | 2014535034 A | 12/2014 |
| JP | 2015031630 | 2/2015 |
| JP | 2015087184 A | 5/2015 |
| JP | 2015516072 | 6/2015 |
| WO | 8601897 A1 | 3/1986 |
| WO | 9941600 A1 | 8/1999 |
| WO | 0136960 | 5/2001 |
| WO | 0171337 A1 | 9/2001 |
| WO | 2005108973 B1 | 11/2005 |
| WO | 2006096243 A1 | 9/2006 |
| WO | 2007058926 | 5/2007 |
| WO | 2008062887 A1 | 5/2008 |
| WO | 2009000793 A1 | 12/2008 |
| WO | 2010010316 A1 | 1/2010 |
| WO | 2010012809 A2 | 2/2010 |
| WO | 2010055823 A1 | 5/2010 |
| WO | 2010097269 A1 | 9/2010 |
| WO | 2010103098 | 9/2010 |
| WO | 2012050803 A2 | 4/2012 |
| WO | 2013004760 A1 | 1/2013 |
| WO | 2013165817 A1 | 11/2013 |
| WO | 2014030615 A1 | 2/2014 |
| WO | 2015068082 A1 | 5/2015 |
| WO | 2015126787 A1 | 8/2015 |

OTHER PUBLICATIONS

International Search Report for International Application No. PCT/US17/12924, dated Apr. 3, 2017, 3 pages.

(56) References Cited

OTHER PUBLICATIONS

Written Opinion of the International Search Authority for International Application No. PCT/US17/12924, dated Apr. 3, 2017, 10 pages.
Nieto et al. "TTU Phased Array: Quality and Productivity", 6th International Symposium on NDT in Aerospace, Nov. 12-14, 2014, Madrid, Spain—www.ndt.net/app.aeroNDT2014, 9 pages.
Schwabe et al. "Ultrasonic Testing Machines with Robot Mechanics—A New Approach to CFRP Component Testing", 2nd International Symposium on NDT in Aerospace 2010—Mo.4.A.3, 5 pages.
European Search Report for EP 14159097, dated Aug. 13, 2014, 5 pages.

* cited by examiner

INSPECTION DEVICES AND RELATED SYSTEMS AND METHODS

TECHNICAL FIELD

Embodiments of the present disclosure relate to inspection devices for use in inspecting one or more structures. More particularly, embodiments of the present disclosure relate to inspection devices including at least one chamber in a housing of the device holding a transducer and at least one coupling material passage defined in the housing and related systems and methods.

BACKGROUND

Nondestructive inspection (NDI) of structures involves thoroughly examining a structure without harming the structure or requiring significant disassembly of the structure. Nondestructive inspection is typically preferred to avoid the potential for damaging the structure. Nondestructive inspection is advantageous for many applications in which a thorough inspection of the exterior and/or interior of a structure is required. For example, non-destructive inspection is commonly used in the aircraft industry to inspect aircraft structures for any type of internal or external damage to, or flaws in, the structure. Inspection may be performed during manufacturing of a structure and/or once a structure is in service. For example, inspection may be required to validate the integrity and fitness of a structure for continued fitness for use in subsequent manufacturing and\or assembly processes, as well as for future ongoing use in service, either periodically or subsequent to an event potentially causing damage to the structure.

Among the structures that are routinely nondestructively tested are composite structures, such as composite sandwich structures and other adhesive bonded panels and assemblies. In particular, composite structures are commonly used throughout the aircraft industry because of the engineering qualities, design flexibility and low weight of composite structures, such as the stiffness-to-weight ratio of a composite sandwich structure. It is frequently desirable to inspect composite structures to identify any flaws, such as cracks, voids or porosity, which could adversely affect the performance of the composite structure. For example, typical flaws in composite materials or composite sandwich structures, which are generally made of one or more layers of lightweight honeycomb or foam core material with composite or metal skins bonded to each side of the core, may include defects in bonds that occur at the interfaces between layers of the composite materials or between the core and the composite skins.

Various types of sensors may be used to perform nondestructive inspection. One or more sensors may be moved over or along the portion of the structure to be examined, and receive data regarding the structure. For example, a pulse-echo, through-transmission, or shear wave sensor may be used to obtain ultrasonic data regarding the structure, such as for thickness gauging, detection of laminar defects and porosity, and/or crack detection in the structure. Resonance, pulse echo, or mechanical impedance sensors may be used to provide indications of voids or porosity, such as in adhesive bond lines of the structure. High resolution inspection of aircraft structure are commonly performed using semi-automated ultrasonic testing (UT) to provide a plan view image of the part or structure under inspection. While solid laminates may be inspected using one-sided pulse echo ultrasonic testing, composite sandwich structures typically require through-transmission ultrasonic testing to achieve high resolution inspection. In through-transmission ultrasonic inspection, ultrasonic sensors such as transducers, or a transducer and an associated receiver sensor, are positioned in mutually facing relationship, contacting opposite sides of the structure to be inspected such as opposite surfaces of a composite material. An ultrasonic signal is transmitted by at least one of the transducers, propagated through the structure, and received by the other transducer or receiver sensor.

Ultrasonic testing generally requires a coupling material (e.g., a fluid, such as water) to aid transmission of the ultrasonic energy to the test specimen because the acoustic impedance mismatch between air and solids (i.e., the test specimen) is unacceptably large. This mismatch causes reflection of the sound waves and a loss in scan quality if a coupling material is not used. In order effectively pass the ultrasonic signal to the structure to be inspected, the coupling material is generally required to be uniform in order to successfully pass the signal through the coupling material without altering the signal. For example, when a flowing fluid, such as water, is utilized as a coupling material, flow of the fluid should be in a substantially laminar regime in order to effective pass the ultrasonic signal to the structure to be inspected without substantially altering the ultrasonic signal.

Furthermore, ultrasonic testing may be limited in terms of inspection speed as many sensors scan only one point or one small area at time. In an ultrasonic inspection involving scanning only one point or one small area at time, the amount of time and resources spent to inspect relatively larger structures, such as aircraft structures, may be undesirable or impractical.

BRIEF SUMMARY

In some embodiments, the present disclosure comprises an inspection device including a housing having a first end, a second end, and a longitudinal axis extending between the first end and the second end. The housing comprises a nozzle portion having at least one opening at the first end. The inspection device further includes a transducer disposed in a rear chamber of the housing proximate the second end. The inspection device further includes at least one fluid channel defined in the housing and extending along at least a portion of the rear chamber. The at least one fluid channel is configured to supply a fluid into a forward chamber of the housing proximate at least one of a signal emitting portion or a signal receiving portion of the transducer.

In further embodiments, the present disclosure comprises a non-destructive inspection (NDI) system including an inspection device where the controller is configured to move the at least one inspection device relative to a structure to be inspected. The inspection device includes a housing having a first end, a second end, and a longitudinal axis extending between the first end and the second end. The housing may include at least one nozzle opening in the housing at the first end of the housing. The inspection device further includes a transducer disposed within a rear chamber of the housing proximate the second end of the housing. The housing has at least one fluid channel defined in the housing and is configured to supply a fluid into a forward chamber of the housing. The at least one fluid channel extends around at least a portion of the transducer. The at least one fluid channel further extends into the forward chamber of the housing at an end of the transducer.

In yet further embodiments, the present disclosure comprises a method of operating an inspection device. The method includes flowing fluid from a fluid inlet in a housing of the inspection device around a transducer in the housing through a plurality of channels surrounding the transducer and redirecting the fluid into a forward chamber of the housing at a portion of the transducer configured to at least one of transmit or receive ultrasonic signals. The method further includes directing the fluid out of a nozzle portion of the housing onto a structure to be inspected and at least one of transmitting or receiving signals with the transducer through the fluid to the structure to be inspected.

DETAILED DESCRIPTION

Inspection devices for use in inspecting (e.g., nondestructive inspection) one or more structures, such as, for example, composite structures (e.g., composite aircraft parts) are described, as are inspection systems and assemblies including inspection devices, and methods of inspecting a structure. In some embodiments, an inspection device may include a housing having at least one chamber in which a transducer (e.g., an ultrasonic transducer for emitting and/or receiving signals) is disposed. The housing may further define at least one passage through which a coupling material (e.g., a fluid) may be passed.

As used herein, the term "substantially" utilized in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

Figure 1:
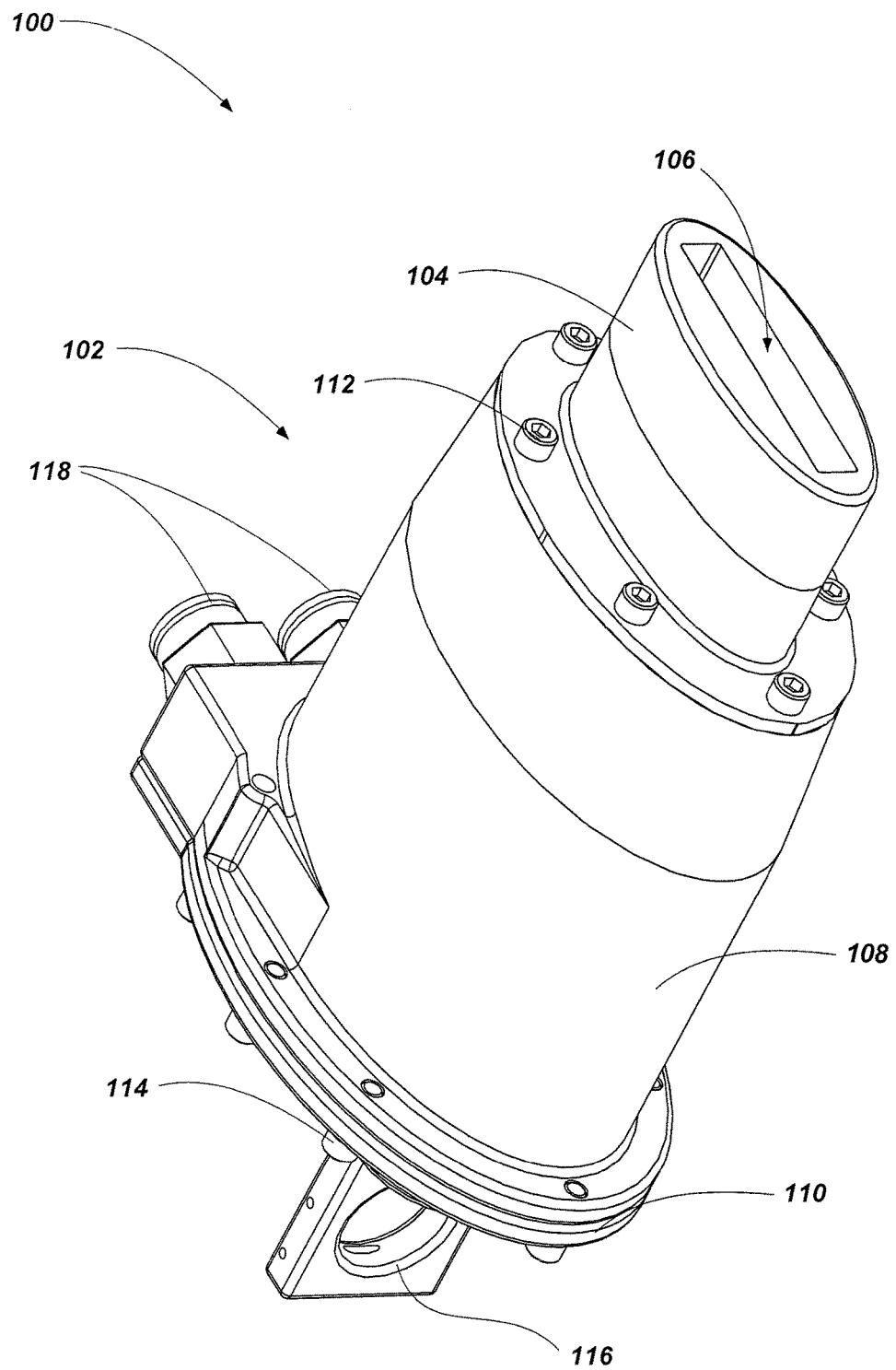
FIG. 1 is an isometric view of an inspection device in accordance with an embodiment of the present disclosure.

FIG. 1 shows an isometric view of an embodiment of an inspection device 100 (e.g., a squirter nozzle). Referring to FIG. 1, the inspection device 100 includes a housing 102 (e.g., the housing comprising a front nozzle portion, a middle portion, and a back end portion, as discussed below). The housing includes a first, forward end (e.g., nozzle portion 104) configured to be positioned proximate the structure to be inspected having an opening 106 defined in the nozzle portion 104. The opening 106 in the nozzle portion 104 may be in communication with a cavity or opening in the housing 102, as discussed below, and may at least partially define a passage through which a coupling material (e.g., a fluid, such as water) may be passed from the housing 102 toward (e.g., onto) the structure to be inspected in order to pass one or more ultrasonic signals between the inspection device 100 and the structure to be inspected (e.g., to transmit and/or received the ultrasonic signals).

As depicted, the opening 106 may exhibit a polygonal shape (e.g., a rectangle). The rectangular shape of the opening 106 may be selected to be complementary to the transducer within the inspection device 100 and to facilitate the desired flow of the fluid from within the housing 102 as the fluid exits the housing 102 through the opening 106, as discussed below in greater detail. In additional embodiments, the opening 106 may exhibit other suitable shapes, such as, for example, other polygonal shapes, elliptical shapes (e.g., circular or oval shapes), combinations thereof, etc. In yet additional embodiments, the opening 106 may be formed as an array of discrete openings.

The housing 102 may include a middle portion 108 housing a transducer (e.g., an ultrasonic transducer for emitting and/or receiving signals), as discussed in further detail below, and a back end portion 110.

In some embodiments, one or both of the nozzle portion 104 and the back end portion 110 may be removably coupled to the middle portion 108 of the housing 102. For example, the nozzle portion 104 may be removably coupled to the middle portion 108 of the housing 102 by one or more fasteners 112. The removable nozzle portion 104 may enable the ability to utilize multiple nozzle portions 104 having various different configurations interchangeably with the remainder of the housing 102. For example, nozzle portions 104 having varying sizes (e.g., a length extending away from the middle portion 108), opening 106 sizes or configurations (e.g., as discussed above), or combinations thereof may be interchangeably coupled to the middle portion 108 of the housing 102 depending on the application. By way of further example, the back end portion 110 may be removably coupled to the middle portion 108 of the housing 102 by one or more fasteners 114. The removable back end portion 110 may enable access to internal components of the inspection device 100, as discussed below in greater detail.

In additional embodiments, one or both of the nozzle portion 104 and the back end portion 110 may be integral to the housing 102 (e.g., one or more of the portions of the housing 102 may form a monolithic structure).

The housing 102 may include a bracket 116 extending from the housing 102 (e.g., from the back end portion 110) for mounting the inspection device 100 to another structure. For example, the bracket 116 may be utilized to mount the inspection device 100 to a robotic arm, a gantry, or other structure configured to move the inspection device 100 in one or more axes relative to the structure to be inspected.

The housing 102 may include one or more inlets 118 for supplying the coupling material (e.g., fluid) to the inspection device 100. For example, one or more inlets 118 (e.g., two inlets) may be positioned proximate to each other on one side of the housing 102 and may be coupled to a fluid source.

Figure 2:
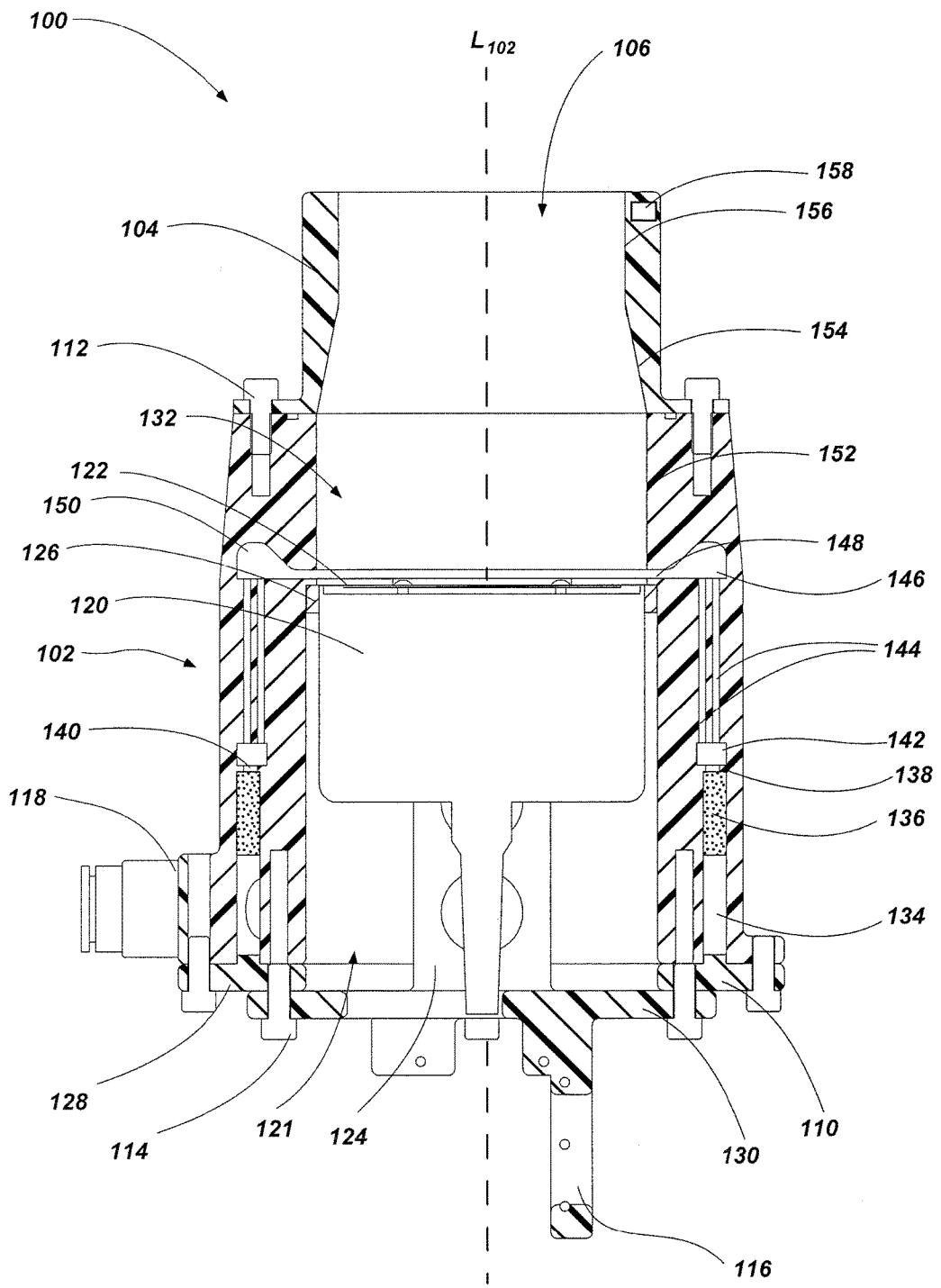
FIG. 2 is a partial cross-sectional side view of the inspection device of FIG. 1 taken along a longitudinal axis of the inspection device.

FIG. 2 is a partial cross-sectional side view of the inspection device 100 of FIG. 1 taken along a longitudinal axis $L_{102}$ (e.g., centerline) of the housing 102 of the inspection device 100. As shown in FIG. 2, a transducer 120 (e.g., an ultrasonic transducer for emitting and/or receiving signals) is positioned within the housing 102 (e.g., in a back chamber 121 defined by the housing 102). In some embodiments, the transducer 120 may comprise a phased array transducer 120 for emitting and/or detecting a plurality of signals (e.g., ultrasound signals). For example, the transducer 120 may be capable of emitting and/or detecting a plurality of signals with a plurality of transducer elements (e.g., 32 elements, 64 elements, etc.) arranged along a line or plane in a direction transverse (e.g., perpendicular) to the longitudinal axis $L_{102}$ of the housing 102. The length and width of the line or plane of the elements of the transducer 120 may correspond to the length and width of the opening 106 such that signals from the transducer are not blocked or reflected by the housing 102 (e.g., by the nozzle portion 104) and may be transmitted to and from the structure to be inspected.

In some embodiments, the transducer 120 may include one or more lenses 122 (e.g., separate from or integral with the transducer 120) that may act to focus the signals produced by the transducer 120. For example, lenses 122 on each element of the transducer 120 may act to focus signals emitted from each element of the transducer 120 by narrowing the width of each signal (e.g., in a direction transverse (e.g., perpendicular) to the longitudinal axis $L_{102}$ of the housing 102) to produce a substantially linear beam of signals as the beam is passed through the opening 106 of the nozzle portion 104 (e.g., which exhibits a complementary rectangular shape).

In some embodiments, the transducer 120 may be mounted to a bracket 124, which may be integral with or separate from the bracket 116, to secure the transducer 120 within the housing 102. Mount 126 may be coupled to the bracket 124, surround the transducer 120, and abut with a portion of the housing 102 to at least partially (e.g., entirely) form a seal around the transducer 120 to reduce (e.g., substantially prevent) the coupling material from flowing around the transducer 120 in a direction toward the back end portion 110 and into the back chamber. In some embodiments, the mount 126 may be formed of multiple pieces (e.g., two) to fit around and secure the transducer 120 within the housing 102.

As depicted, the back end portion 110 may include one or more plates coupled to the housing 102 (e.g., the middle portion 108 of the housing 102). For example, a first plate 128 of the back end portion 110 may be coupled to the middle portion 108 of the housing 102 and a second plate 130 of the back end portion 110 (e.g., having the bracket 116 coupled thereto or formed integral therewith) may be coupled to one or more of the first plate 128 and the middle portion 108 of the housing 102.

As discussed above, the housing 102 may include inlets 118 for supplying the coupling material (e.g., fluid) to the inspection device 100 from a fluid source. The inlets 118 are placed in communication with a fluid source to provide a flow of fluid into forward chamber 132 while the inspection device 100 is in use. The inlets 118 are in communication (e.g., fluid communication) with a first fluid chamber 134 positioned at a location distal to the opening 106 in the nozzle portion 104. The first fluid chamber 134 may extend at least partially around the housing 102. For example, the first fluid chamber 134 may exhibit an annular shape extending about an entirety of the housing 102 (e.g., around or about back chamber 121).

As depicted, the inlets 118 may flow directly into the first fluid chamber 134. In additional embodiments (e.g., where the inlets 118 are positioned relatively closer the opening 106), an additional fluid pathway may extend between the inlets 118 and the first fluid chamber 134 to direct fluid to the first fluid chamber 134 in a direction away from the opening 106.

In some embodiments, the removable back end portion 110 (e.g., the first plate 128) may define a portion of the first fluid chamber 134. For example, the first plate 128 may be removed in order to provide access the first fluid chamber 134.

In some embodiments, a filter material 136 may be disposed in the first fluid chamber 134 to at least partially reduce the amount of any contaminants in the fluid passing through the housing 102. For example, filter material 136 may substantially fill the first fluid chamber 134. In some embodiments, the removable first plate 128 may be utilized to access the first fluid chamber 134 to install, service, and/or replace the filter material 136.

A parting wall 138 having one or more openings 140 defined therein may be positioned on a downstream side of the first fluid chamber 134 (e.g., an outlet). For example, the openings 140 in the parting wall 138 may have a size (e.g., cross-section area, diameter) that is less than a size (e.g., cross-section area, diameter) of the first fluid chamber 134. The parting wall 138 may act to separate the first fluid chamber 134 from a second fluid chamber 142. Similar to the first fluid chamber 134, the second fluid chamber 142 may exhibit a substantially annular shape extending around the housing 102. In some embodiments, the parting wall 138 may be integral to the middle portion 108 of the housing 102.

Figure 3:
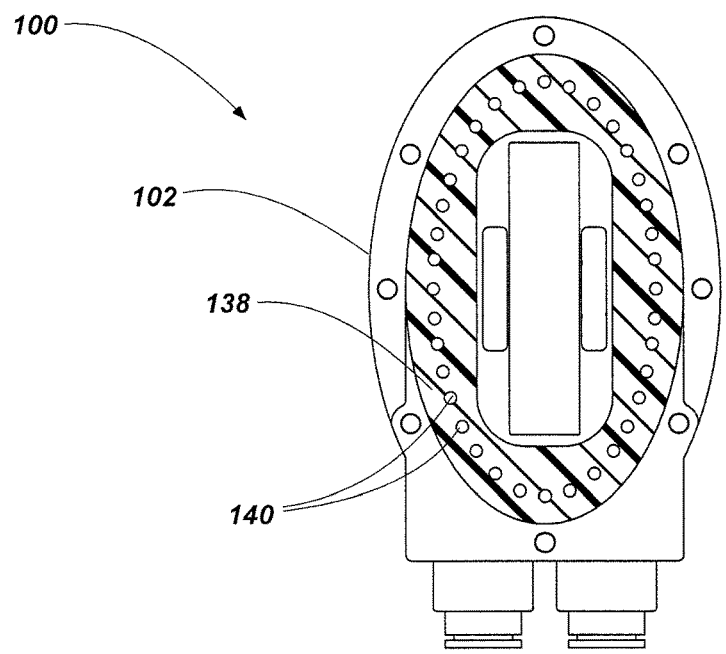
FIG. 3 is a partial cross-sectional front view of the inspection device of FIG. 1 taken along a lateral axis of the inspection device.

FIG. 3 is a partial cross-sectional front view of the inspection device 100 of FIG. 1 taken along a lateral axis of the inspection device 100 (e.g., in a direction perpendicular to the longitudinal axis $L_{102}$ of the housing 102). As shown in FIG. 3, the openings 140 in the parting wall 138 may be defined in the parting wall 138 as a plurality of elliptical openings 140 (e.g., circular) having substantially equally spacing between each opening 140.

Referring back to FIG. 2, a downstream side of the second fluid chamber 142 (e.g., an outlet) may be in communication with a plurality of channels 144. The channels 144 may have a total size (e.g., cross-section area, diameter) that is substantially less than (e.g., 50% or less) than an overall or total size (e.g., cross-section area) of the first fluid chamber 134 and/or second fluid chamber 142. The relatively smaller channels 144 my act to constrict (e.g., reduce the flow rate) the flow from one or more of the inlets 118 and fluid chambers 134, 144 into the forward chamber 132. As discussed below, such limiting of the flow rate may act to increase the probability of avoiding turbulence in the flow through the housing 102. In other words, by restricting the volumetric flow rate through at least a portion of the housing 102 (e.g., through channels 144), the flow through the housing 102 may be substantially maintained in a laminar flow regime.

In some embodiments, the parting wall 138 may act to contain the filter material 136 in the first fluid chamber 134. For example, the parting wall 138 may at least partially (e.g., entirely) isolate the filter material 136 in the first fluid chamber 134 to prevent the filter material 136 from contacting and/or obstructing the channels 144.

Figure 4:
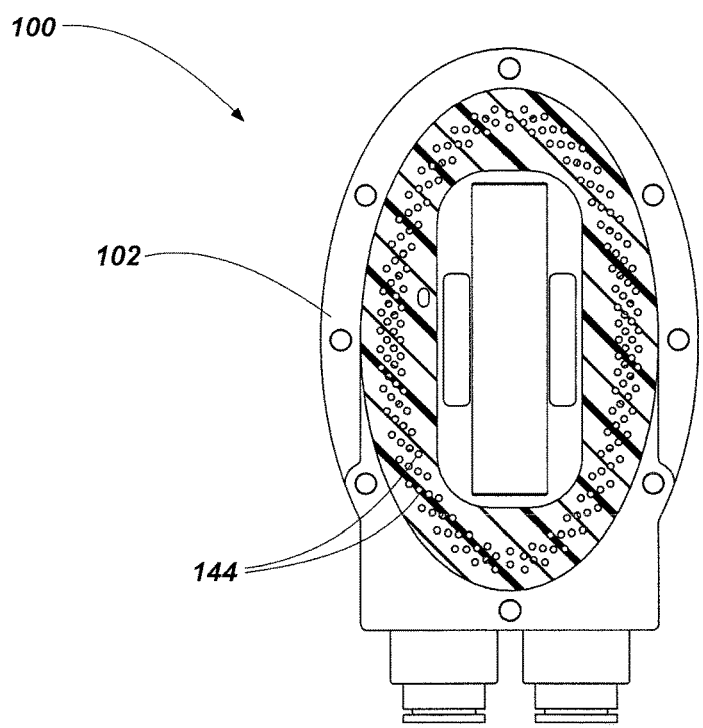
FIG. 4 is yet another partial cross-sectional front view of the inspection device of FIG. 1 taken along a lateral axis of the inspection device.

FIG. 4 is another partial cross-sectional front view of the inspection device 100 of FIG. 1 taken along another lateral axis of the inspection device 100 (e.g., in a direction perpendicular to the longitudinal axis $L_{102}$ of the housing 102). As shown in FIG. 4, the channels 144 are defined as a series of elliptical (e.g., circular) apertures extending through the housing 102. For example, the channels 144 may be arranged along one or more concentric circles (e.g., four concentric circles).

Referring back to FIG. 2, a downstream side of the channels 144 (e.g., an outlet) may be in communication with a third fluid chamber 146. Similar to the first and second fluid chambers 134, 142, the third fluid chamber 146 may exhibit a substantially annular shape extending around the housing 102 (e.g., around or about the forward chamber 132).

A downstream side of the third fluid chamber 146 (e.g., an outlet) may be in communication the forward chamber 132 via one or openings (e.g., a redirect passage). For example, a slot 148 (e.g., an annular slot) may extend around or about forward chamber 132 and be in communication (e.g., direct commination) with the forward chamber 132 to supply fluid to be dispensed from the housing 102 via the nozzle portion 104. In some embodiments, the third fluid chamber 146 may exhibit an enlarged portion 150 (e.g., bulbous in cross section portion) upstream (e.g., radially or laterally outward) from the slot 148. For example, the enlarged portion 150 may have a depth (e.g., taken in a direction along the longitudinal axis $L_{102}$ of the housing 102) that is greater than a depth (e.g., taken in the same direction) of the slot 148. The relatively smaller slot 148 may act to constrict (e.g., reduce the flow rate) the flow from the third fluid chamber 146 into the forward chamber 132. As discussed above and below, such limiting of the flow rate may act to increase the probability of avoiding turbulence in the flow through the housing 102 (e.g., as fluid enters the forward chamber 132).

Figure 5:
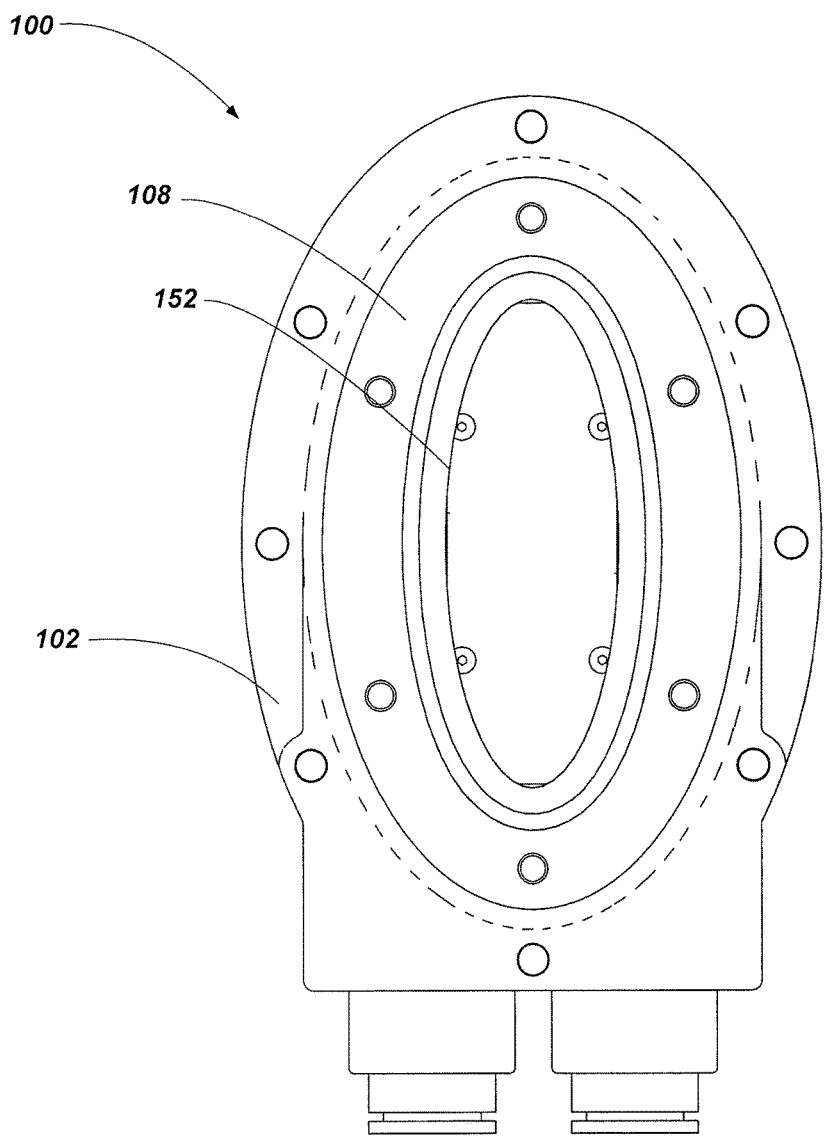
FIG. 5 is front view of a portion of the inspection device of FIG. 1.

FIG. 5 is front view of a portion of the inspection device 100 of FIG. 1 (e.g., the housing 102 with the nozzle portion 104 removed). As shown in FIGS. 2 and 5, a portion of the forward chamber 132 (e.g., an innermost portion proximate or bordering the transducer 120) in the housing 102 may exhibit a substantially elliptical (e.g., oval) cross section. For example, an inner sidewall 152 of the middle potion 108 of the housing 102 may exhibit a continuous curved shape extending around or about an outer circumference of the forward chamber 132 to define the oval cross section.

Referring back to FIG. 2, another portion of the forward chamber 132 (e.g., an innermost portion of the nozzle portion 104) in the housing 102 may exhibit a transition from the cross section of an inner portion of the forward chamber 132 (e.g., the oval cross section) to a different cross section. For example, a transition sidewall 154 of the housing 102 (e.g., of the nozzle portion 104) may gradually transition (e.g., along a select length) from the oval cross section to another cross section of an outer portion (e.g., outmost portion) of the nozzle portion 104 (e.g., opening 106). In some embodiments, the transition sidewall 154 may gradually transition in a tapering manner to the rectangular cross section of the opening 104 as shown in FIG. 1.

As depicted in FIG. 2, the nozzle portion 104 may include a rectangular sidewall 156 positioned adjacent to and contiguous with the transition sidewall 154. Each of the inner sidewall 152, the transition sidewall 154, and the rectangular sidewall 156 may extend along a select length of the longitudinal axis $L_{102}$ of the housing 102 to provide a gradual transition between cross-sectional areas of the housing 102 through which may fluid flow. For example, moving from an inner portion of the forward chamber 132 to the opening 106 in the nozzle portion 104, the inner cross section of the housing 102 may gradually transition from an elliptical (e.g., an oval, having smooth edges) cross section to a polygonal (e.g., a rectangle, having discontinuous edge or corners) cross section. Such a gradual cross-sectional transition may act to substantially avoid any abrupt transition that may cause irregularities in the flow (e.g., turbulent flow). In some embodiments, each of the inner sidewall 152, the transition sidewall 154, and the rectangular sidewall 156 may extend along at least 0.25 inch (6.35 millimeters) of the longitudinal axis $L_{102}$ of the housing 102 (e.g., between 0.25 inch (6.35 millimeters) and 1 inch (25.4 millimeters)).

In some embodiments, the nozzle portion 104 of the housing 102 may comprise a flexible material (e.g., one or more of a polymer, an elastomer, and/or a rubber) that is adapted to deform (e.g., elastically deform) in a situation where the housing 102 contacts another structure (e.g., the structure to be inspected). Such an embodiment may act to protect the structure and the inspection device 100 from damage (e.g., to minimize such damage) should contact occur between these structures. For example, the nozzle portion 104 may comprise a material exhibiting a relatively low hardness, such as a rubber material having a durometer of 45 to 85 (e.g., 45 to 50, 57 to 63, 68 to 72, 80 to 85) on the Shore A scale. In some embodiments, the nozzle portion 104 may comprise a material exhibiting a relatively lower hardness as compared to another part of the housing 102 (e.g., the middle portion 108). For example, the middle portion 108 may comprise a polymer material (e.g., acrylonitrile butadiene styrene (ABS)) having a durometer on the Shore D scale (e.g., 75 to 90 on the Shore D scale) while the relatively more flexible nozzle portion 104 (e.g., comprising a polymer or rubber) exhibits a substantially lower durometer of on the Shore A scale (less than 85 on the Shore A scale).

In some embodiments, a portion of the housing 102 (e.g., the nozzle portion 104) may include one or more sensors (e.g., sensor 158) disposed on or in the housing 102 (e.g., on or within the nozzle portion 104 comprising a flexible material) positioned and configured to sense a force applied to the nozzle portion 104. For example, sensor 158 may comprise a load sensor (e.g., strain gauge) to sense one or more forces applied to the nozzle portion 104 (e.g., force (e.g., tension, compression) in the nozzle portion 104 due to deformation of the nozzle portion 104). The sensor 158 may be utilized to detect force applied to the nozzle portion 104 when the inspection device 100 has contacted another object (e.g., the structure to be inspected) and enable the operator (e.g., a human or a computer, via a closed loop) to take appropriate action to minimize damage caused by the contact.

Figure 6:
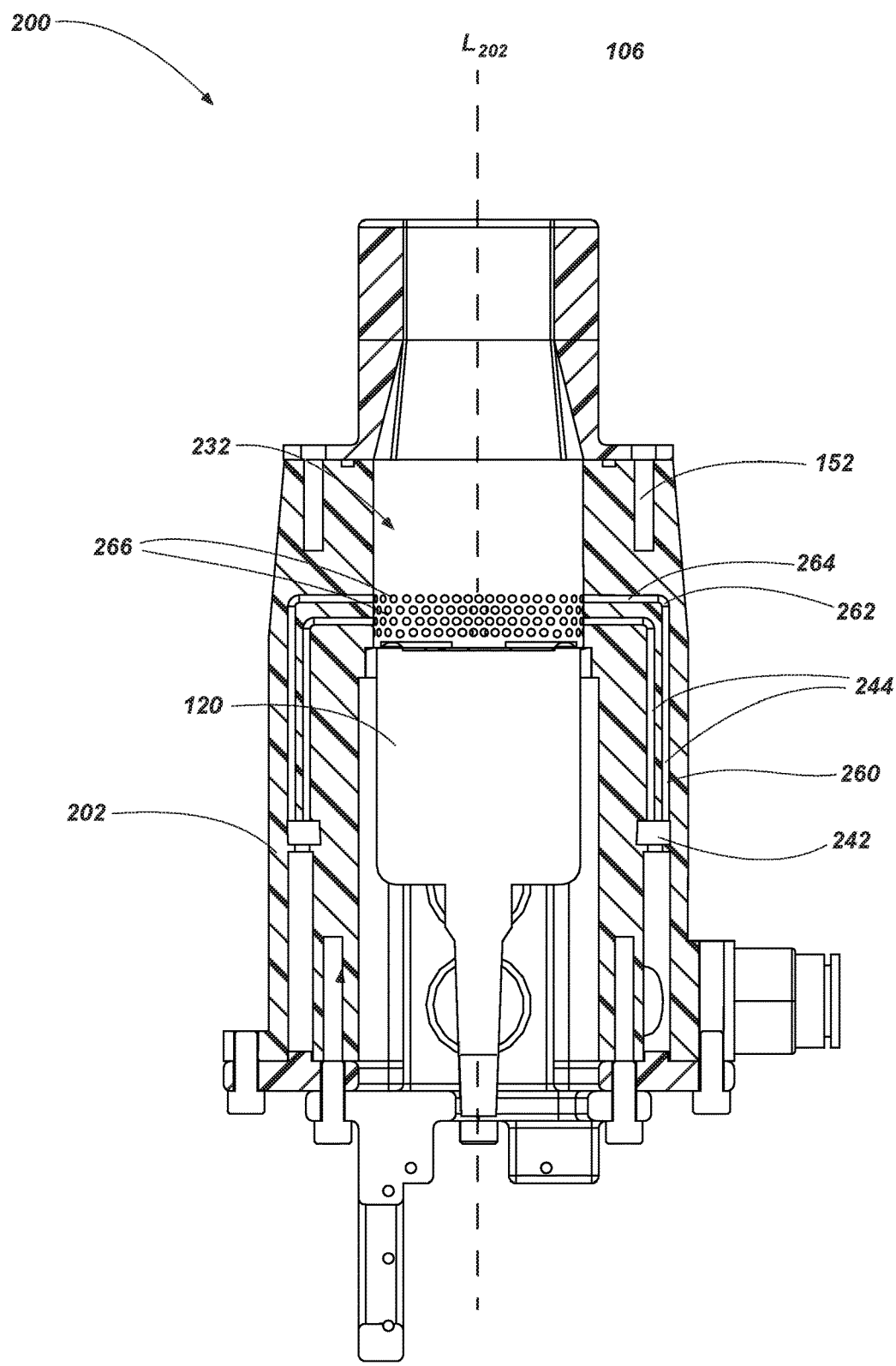
FIG. 6 is a partial cross-sectional side view of an inspection device in accordance with an embodiment of the present disclosure.

FIG. 6 is a partial cross-sectional side view of an embodiment of an inspection device 200. Inspection device 200 may be similar to and include one or more of the same features and functioning as inspection device 100 discussed above with reference to FIGS. 1 through 5. As shown in FIG. 6, inspection device 200 may include a housing 202 having channels 244 therein, which may be somewhat similar to the channels 144 in housing 102 discussed above in relation to FIG. 2. However, channels 244 may extend from a second fluid chamber 242 to forward chamber 232 of the housing 202. For example, channels 244 may extend directly (e.g., uninterrupted) from a second fluid chamber 242 to forward chamber 232 of the housing 202 (e.g., without a relatively larger fluid chamber being disposed between the second fluid chamber 242 and the forward chamber 232). For example, one or more of the channels 244 (e.g., each channel 244) may comprise a first linear portion 260 extending in a direction along (e.g., directly along or substantially parallel to) a longitudinal axis $L_{202}$ of the housing 202, a redirecting portion 262 (e.g., an elbow), and a second linear portion 264 (e.g., a redirecting passage) extending in a direction transverse to (e.g., substantially perpendicular to) the longitudinal axis $L_{202}$ of the housing 202. The channels 244 may each enter into the forward chamber 232 of the housing 202 through apertures 266 (e.g., defining an outlet of the channels 244) in the housing 202 to supply fluid into the forward chamber 232 of the housing 202. For example, apertures 266 may be positioned proximate (e.g., at the transducer 120) and may extend about (e.g., surround) a portion the forward chamber 232 of the housing 202 (e.g., aligned in a concentric pattern similar to the channels 244) in order to supply fluid into the forward chamber 232 of the housing 202.

Figure 7:
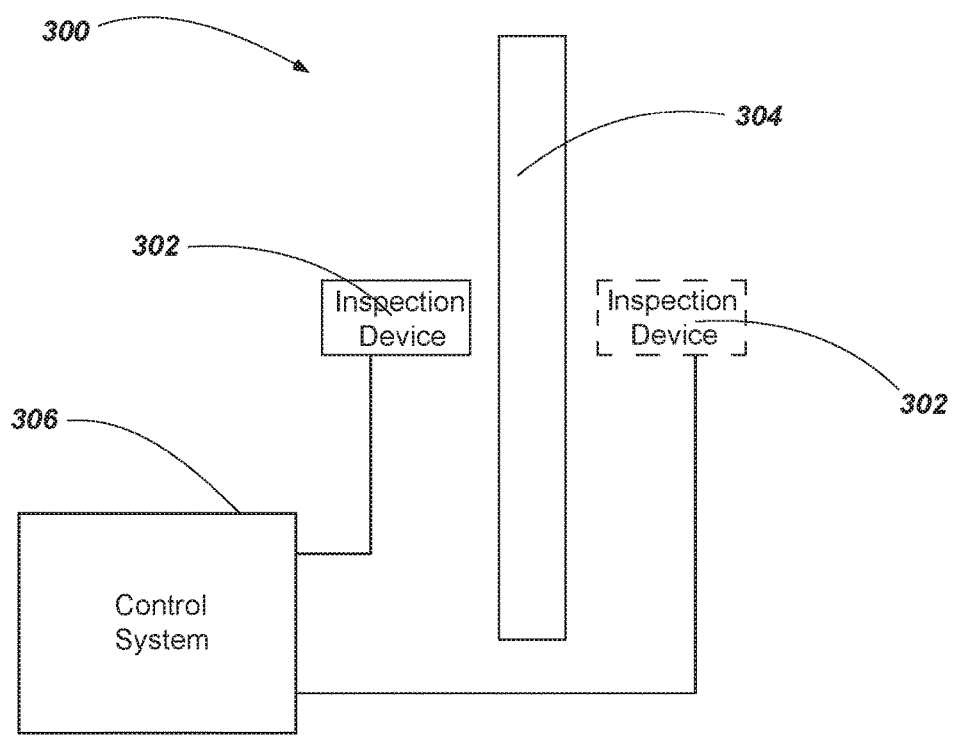
FIG. 7 is a schematic view of an inspection system in accordance with an embodiment of the present disclosure.

FIG. 7 is a schematic view of an inspection system 300 implementing one or more inspection devices 302 (e.g., inspection devices 100, 200 discussed above with reference to FIGS. 1 through 6). As depicted, inspection device or devices 302 (e.g., one inspection device in a pulse echo configuration or, optionally, two inspection devices in a through transmission configuration) may be utilized to inspect a structure 304 (e.g., a portion of an aircraft comprising one or more composite materials). In some embodiments, the inspection system 300 may include an array of inspection devices 302 (e.g., three or more). As the inspection device(s) 302 and the structure 304 are moved relative to one another, power and a coupling material is supplied to the inspection device(s) 302 from a control system 306, which may be one or multiple discrete and/or separate components, to couple direct signals (e.g., ultrasonic signals) from the inspection device(s) 302 to the structure via the coupling fluid. The ultrasonic signals resulting from penetration of the structure 304 and at least one of reflection and refraction by elements of structure 304 are detected by the inspection device(s) 302 and sent back to the control system 306 for further processing (e.g., to analyze and identify defects in the structure). The results of the processing may be displayed or otherwise conveyed to a user.

Embodiments of the present disclosure may provide inspection devices that are more robust and effective than other similar inspection devices. For example, inspection devices in accordance with some embodiments of the present disclosure enable implementation of a device having a reduced size (e.g., volume or footprint including an oval inner chamber for suppling coupling fluid to and onto the structure) that can be easily moved around a structure to be inspected. Further, the inspection device enables the use a phased array transducer that may output and/or receive signals passed directly between the transducer and the structure through the coupling fluid supplied by the inspection device without having to otherwise redirect the signals. Further still, the inspection device provides a fluid pathway extending along a majority of the length of the inspection device that is able to direct fluid around the transducer, into a fluid chamber directly in front of the transducer, and out of the housing of the inspection device through a nozzle portion toward and onto a structure to be inspected. Such a configuration ensures that the signals from the transducer are adequately coupled between the inspection device and the structure while reducing or minimizing turbulence in the fluid that may disrupt the signals traveling to and/or from the transducer by substantially maintaining the fluid traveling through and out of the inspection device in a laminar flow regime.

While particular embodiments of the disclosure have been shown and described, numerous variations and alternate embodiments encompassed by the present disclosure will occur to those skilled in the art. Accordingly, the disclosure is only limited in scope by the appended claims and their legal equivalents.

What is claimed is:

1. An inspection device, comprising:
   a housing having a first end, a second end, and a longitudinal axis extending between the first end and the second end, the housing comprising a nozzle portion having at least one opening at the first end, wherein the nozzle portion of the housing comprises a flexible material configured for elastic deformation;
   a transducer disposed in a rear chamber of the housing proximate the second end; and
   at least one fluid channel defined in the housing and extending along at least a portion of the rear chamber, the at least one fluid channel configured to supply a fluid into a forward chamber of the housing proximate at least one of a signal emitting portion or a signal receiving portion of the transducer.

2. The inspection device of claim 1, further comprising at least one fluid inlet positioned at the second end of the housing and in communication with the at least one fluid channel.

3. The inspection device of claim 2, wherein the at least one fluid channel comprises an annular chamber defined by the housing surrounding at least a portion of the rear chamber housing the transducer.

4. The inspection device of claim 3, further comprising at least one filter disposed in the annular chamber.

5. The inspection device of claim 3, wherein the at least one fluid channel further comprises a plurality of channels extending around at least a portion of the rear chamber housing the transducer and extending substantially parallel to the longitudinal axis of the housing, the plurality of channels in communication with and downstream from the annular chamber.

6. The inspection device of claim 5, wherein the at least one fluid channel further comprises at least one redirect passage in communication with and extending between the plurality of channels and the forward chamber, the at least one redirect passage extending at least partially in a direction transverse to the longitudinal axis of the housing and configured to supply fluid from the plurality of channels into the forward chamber.

7. The inspection device of claim 6, wherein an outlet of the at least one redirect passage is positioned proximate the at least one of the signal emitting portion or the signal receiving portion of the transducer.

8. The inspection device of claim 6, wherein the at least one redirect passage comprises a continuous annular slot extending around and surrounding a circumference of the forward chamber, the annular slot being in communication with an outlet of each channel of the plurality of channels.

9. The inspection device of claim 6, wherein the at least one redirect passage comprises another plurality of channels surrounding the forward chamber, each channel of the another plurality of channels being in communication with one corresponding channel of the plurality of channels.

10. The inspection device of claim 1, wherein a portion of an interior wall of the housing defining the forward chamber comprises an elliptical cross section.

11. The inspection device of claim 10, wherein another portion of the interior wall of the housing defining the opening at the first end of the housing comprises a rectangular cross section, and wherein a transition portion of the interior wall of the housing extending between the portion of the interior wall of the housing comprising the elliptical cross section and the another portion of the interior wall of the housing comprising the rectangular cross section comprises a cross section having a gradual transition from the elliptical cross section to the rectangular cross section.

12. The inspection device of claim 1, wherein the nozzle portion of the housing is configured to be nondestructively removed from a remainder of the housing.

13. The inspection device of claim 1, wherein the flexible material of the nozzle portion exhibits a durometer greater than 0 and less than 85 on a Shore A scale.

14. An inspection device, comprising:
- a housing having a first end, a second end, and a longitudinal axis extending between the first end and the second end, the housing comprising a nozzle portion having at least one opening at the first end, wherein the nozzle portion of the housing comprises a flexible material having a durometer that is less than a material forming a remainder of the housing;
- a transducer disposed in a rear chamber of the housing proximate the second end; and
- at least one fluid channel defined in the housing and extending along at least a portion of the rear chamber, the at least one fluid channel configured to supply a fluid into a forward chamber of the housing proximate at least one of a signal emitting portion or a signal receiving portion of the transducer.

15. An inspection device, comprising:
- a housing having a first end, a second end, and a longitudinal axis extending between the first end and the second end, the housing comprising a nozzle portion having at least one opening at the first end, wherein the nozzle portion of the housing comprises at least one sensor configured to detect a force applied to the housing;
- a transducer disposed in a rear chamber of the housing proximate the second end; and
- at least one fluid channel defined in the housing and extending along at least a portion of the rear chamber, the at least one fluid channel configured to supply a fluid into a forward chamber of the housing proximate at least one of a signal emitting portion or a signal receiving portion of the transducer.

16. A non-destructive inspection (NDI) system, comprising:
- a controller; and
- at least one inspection device, the controller configured to move the at least one inspection device relative to a structure to be inspected, the at least one inspection device comprising:
  - a housing having a first end, a second end, and a longitudinal axis extending between the first end and the second end, the housing comprising at least one nozzle opening in the housing at the first end of the housing; and
  - a transducer disposed within a rear chamber of the housing proximate the second end, wherein the housing comprises a plurality of fluid channels defined in the housing and at least partially surrounding the transducer, the plurality of fluid channels configured to supply a fluid into a forward chamber of the housing, the plurality of fluid channels extending around at least a portion of the transducer and extending into the forward chamber of the housing at an end of the transducer, the plurality of fluid channels of the at least one inspection device comprising a redirection portion extending laterally inward in a direction transverse to the longitudinal axis of the housing and opening into the forward chamber of the housing, wherein the redirection portion comprises a plurality of redirect passages and each channel of the plurality of fluid channels is in communication with one redirect passage of the plurality of redirect passages.

17. The non-destructive inspection system of claim 16, wherein a portion of the housing defining the at least one nozzle opening of the at least one inspection device comprises:
- a flexible material configured for elastic deformation and exhibiting a durometer greater than 0 and less than 85 on a Shore A scale; and
- at least one sensor configured to detect a compressive force applied to the housing proximate the at least one nozzle opening.

18. A method of operating an inspection device, the method comprising:
- flowing fluid from a fluid inlet in a housing of the inspection device around a transducer in the housing through a plurality of channels surrounding the transducer;
- redirecting the fluid into a forward chamber of the housing at a portion of the transducer configured to at least one of transmit or receive ultrasonic signals;
- directing the fluid out of a nozzle portion of the housing onto a structure to be inspected;
- at least one of transmitting or receiving signals with the transducer through the fluid to the structure to be inspected; and
- sensing a deformation of the nozzle portion of the housing with at least one sensor.

19. The method according to claim 18, further comprising maintaining flow of the fluid through the forward chamber of the housing of the inspection device in a substantially laminar flow regime.

20. A non-destructive inspection (NDI) device, comprising:
- a housing having a first end, a second end, and a longitudinal axis extending between the first end and the second end, the housing comprising at least one nozzle opening in the housing at the first end of the housing;
- a transducer disposed within a rear chamber of the housing proximate the second end; and
- a fluid pathway defined in the housing at least partially surrounding the transducer and configured to supply a fluid into a forward chamber of the housing, the fluid pathway comprising:
  - fluid channels having multiple discrete channels positioned adjacent to each other along a lateral axis of the housing in a direction transverse to the longitudinal axis of the housing, the fluid channels extending around at least a portion of the transducer; and
  - a redirection portion comprising a single annular passage that is in communication with each channel of the fluid channels extending laterally inward in the direction transverse to the longitudinal axis of the housing and opening into the forward chamber of the housing, the annular passage having a width along the longitudinal axis of the housing that is greater than a width of each passage of the channels taken in a direction substantially perpendicular to the longitudinal axis of the housing.

21. The inspection device of claim 20, wherein the single annular passage is configured to deliver fluid directly into the forward chamber of the housing.

22. The inspection device of claim 20, wherein an outlet of the single annular passage is positioned proximate at least one of a signal emitting portion or a signal receiving portion of the transducer.

23. The inspection device of claim 20, wherein an outlet of the single annular passage comprises a continuous annular slot extending around and surrounding a circumference of the forward chamber, the annular slot being in communication with an outlet of each channel of the fluid channels.

24. The inspection device of claim 20, wherein the first end of the housing comprises a flexible material configured for deformation.

25. The inspection device of claim 20, wherein the first end of the housing comprises a material having a durometer that is less than a material forming a remainder of the housing.

* * * * *

UNITED STATES PATENT AND TRADEMARK OFFICE
CERTIFICATE OF CORRECTION

PATENT NO. : 10,302,600 B2  
APPLICATION NO. : 15/000921  
DATED : May 28, 2019  
INVENTOR(S) : Jeremy D. Palmer, Ronald G. Mellus and Edwin Dean S. Oba Page 1 of 1

It is certified that error appears in the above-identified patent and that said Letters Patent is hereby corrected as shown below:

On the Title Page  
In ITEM (57)  Line 3,  change "the housing. The" to --a housing. The--

In the Specification  
Column 1, Line 30,  change "and\or assembly" to --and/or assembly--  
Column 2, Line 16,  change "In order effectively" to --In order to effectively--  
Column 2, Line 23,  change "to effective pass" to --to effectively pass--  
Column 2, Line 28,  change "area at time." to --area at a time.--  
Column 2, Line 29,  change "area at time," to --area at a time,--  
Column 4, Line 5,  change "received the" to --receive the--  
Column 5, Line 32,  change "the back chamber." to --the back chamber 121.--  
Column 6, Line 31,  change "substantially equally" to --substantially equal--  
Column 6, Line 40,  change "my act to" to --may act to--  
Column 6, Line 42,  change "144 into the" to --142 into the--  
Column 7, Line 10,  change "commination) with" to --communication) with--  
Column 7, Line 32,  change "potion 108 of" to --portion 108 of--  
Column 7, Line 48,  change "opening 104 as" to --opening 106 as--  
Column 9, Line 3,  change "portion the forward" to --portion of the forward--  
Column 9, Line 39,  change "the use a" to --the use of a--

Signed and Sealed this  
Sixteenth Day of July, 2019

Andrei Iancu  
*Director of the United States Patent and Trademark Office*